United States Patent [19]

Yamada

[11] Patent Number: 4,730,376
[45] Date of Patent: Mar. 15, 1988

[54] BLADE REMOVAL APPARATUS FOR CHANGEABLE BLADE SCALPEL

[75] Inventor: Katsumi Yamada, Seki, Japan

[73] Assignee: Feather Kogyo Kabushiki Kaisha, Mino, Japan

[21] Appl. No.: 932,568

[22] Filed: Nov. 20, 1986

[51] Int. Cl.⁴ .............................................. B23P 19/04
[52] U.S. Cl. ........................................ 29/239; 24/278; 206/355; 206/359
[58] Field of Search ................ 29/235, 239, 270, 278, 29/808; 206/349, 355, 359; 30/339

[56] References Cited

U.S. PATENT DOCUMENTS

| | | | |
|---|---|---|---|
| 3,172,316 | 3/1965 | Grieshaber | 29/270 |
| 3,941,243 | 3/1976 | Yamada et al. | |
| 4,168,777 | 9/1979 | Gaskell et al. | 206/359 |
| 4,180,162 | 12/1979 | Magney | 206/359 |
| 4,270,416 | 6/1981 | Thompson | 29/235 |
| 4,386,457 | 6/1983 | Coombs | 29/235 |
| 4,395,807 | 8/1983 | Eldridge et al. | 29/239 |
| 4,466,539 | 8/1984 | Frauenhoffer | 29/239 |

*Primary Examiner*—Robert C. Watson
*Attorney, Agent, or Firm*—Wenderoth, Lind & Ponack

[57] ABSTRACT

A blade removal apparatus for a changeable blade scalpel in which a blade is removably mounted on a scalpel handle by fitting a mounting hole formed in the blade over a blade mounting part having a narrow width provided on the tip end of the scalpel handle. The blade removal apparatus has a box part having an open top and a side wall and an acceptor part projecting laterally from the upper part of the side wall, and a cover part closing the open top and having a visored part extending over the acceptor part. A guide edge on the acceptor part defines a lower gap tapered so as to become narrower as it extends to the inside of the box part and into which blade mounting parts of changeable blade scalpels of various types can be inserted. The cover part has a stopping stepped part defining an upper gap between the lower surface of the visored part and the guide edge and into which upper gap a blade on a scalpel is insertable. The stopping stepped part has an angle notch engageable by a blade root end edge on a blade, a pair of stoppers projecting from the lower side of the cover part of both sides of the lower gap, and a push button which can be pushed down from the cover into the box part and having a pair of projection pieces which, make contact with the stoppers for forcing the blade surface located on both sides of the blade mounting part on the scalpel down for lifting the blade root end edge of the blade and thereby causing the blade root and edge to be engaged with the angle notch of the stopping stepped part.

3 Claims, 16 Drawing Figures

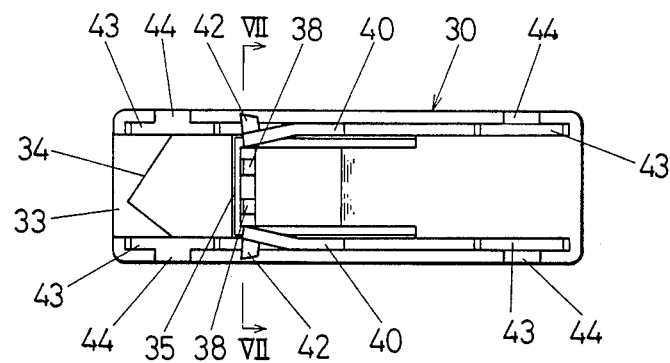
FIG.6
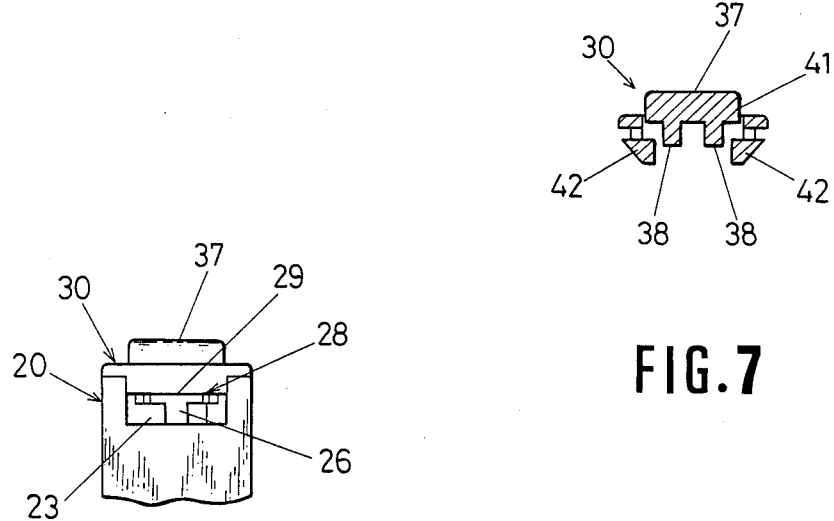
FIG.7
FIG.8

BLADE REMOVAL APPARATUS FOR CHANGEABLE BLADE SCALPEL

BACKGROUND OF THE INVENTION

1. Field of the Invention

The present invention relates to a blade removal apparatus for a changeable blade scalpel for removing a used blade from a scalpel handle when the blade of the changeable blade scalpel is to be replaced.

2. Description of the Prior Art

Conventionally, when a changeable blade scalpel for surgical use gets to be useless, it is necessary to remove a used blade from the scalpel handle and replace it. In changing this blade for a new one, it is relatively easy to fit the blade root of the new blade to a blade mounting portion of the scalpel handle at a mounting position thereof, and hence the change can be effected manually. However, to remove the used blade from the changeable blade scalpel it is necessary to push the used blade root up from the blade mounting portion and draw the used blade from a stopper groove in the blade mounting portion of the same handle. Accordingly, much labor is required in manual handling, and the operator's hand may be injured. Therefore, various types of blade removal apparatus have been devised. Particularly, among them, Australian Pat. No. 25594-77 shows in FIGS. 12 to 14 a technique known in foreign countries. The blade removal apparatus R of this patent has a T-shaped insertion hole E formed in one side of a box thereof, into which hole the blade tip of a changeable blade scalpel is inserted, and it furthermore has a stopping stepped edge D having a slope slanted interiorly thereof on the end edge of a visored portion of a top thereof projecting from the side surface described above. The blade is removed by inserting the tip of the blade scalpel into the insertion hole E and pushing the scalpel handle up around the lower surface of the stopper stepped edge D, pulling the handle toward the operator while freeing the blade root end of the blade scalpel from the base end of the handle, and engaging the freed end on the inner surface of the stopping stepped edge D. In addition, another example of such a blade removal apparatus is known as a universal scalpel blade remover R1 disclosed in English Design Resistration No. 986074, which is here illustrated in FIGS. 15 and 16. It is adapted to push down a visored portion which projects from the upper surface of one side of a box-shaped vessel B having a rectangular cross section, push the base end part of a scalpel handle down to a lower groove of a T-shaped groove E1 instead of pushing the scalpel handle up around the lower surface of a stopping stepped edge D1 provided on the tip end of the visored portion C1, free the blade root end of a used blade on a blade scalpel from the base end, and thereafter the scalpel handle is pulled toward the operator for removal of the blade. Here, the vessel B is adapted to be higher in its height for receiving the removed blade therein.

These prior blade removal apparatuses, as described above, require much labor and are not constructed so simply as to allow the blade to be pulled out at a touch, because, for removing the used blade the scalpel handle must be engaged on the visored portion by handling by the operator's fingers to pull out the used blade.

SUMMARY OF THE INVENTION

In view of the drawbacks of the prior techniques, it is an object of the present invention to provide an improved blade removal apparatus for a changeable blade scalpel which is employed in a surgical operation for patients and the like.

Another object of the present invention is to provide a blade removal apparatus for a changeable blade scalpel wherein the changeable blade scalpel is inserted into a gap formed in an acceptor of the changeable blade removal apparatus and a push button is pushed down, whereby only the used blade is pushed down for facilitating the used blade to slip out of the change blade scalpel.

Still another object of the present invention is to provide a blade removal apparatus for a changeable blade scalpel which includes an insertion portion into which a blade mounting part is insertable whereby the removal apparatus can be made applicable to changeable blade scalpels of various sizes even if the blade mounting part of the change blade scalpel has various sizes.

Yet still another object of the present invention is to provide a blade removal apparatus for a changeable blade scalpel capable of securely housing a used blade removed from the changeable blade scalpel.

To achieve the above objects of the present invention, a blade removal apparatus comprises: (a) a box part having a rectangular cross section, and including an open upper side and an acceptor portion provided on the upper part of longitudinal side thereof projecting from the side surface thereof; (b) a cover part having a visored portion for covering the acceptor portion thereof and fitted to the upper part of the box for covering the opening therewith; (c) a guide edge formed on the acceptor portion which is tapered to become narrower as it goes interiorly thereof and having a gap in the inside end part of the acceptor portion into which gap each of blade mounting parts of various changeable blade scalpels can be inserted; (d) a stopping stepped part having a T-shaped gap formed between the guide edge and the lower surface of the visored portion of the cover, into which the change blade can be inserted, and having an notch capable of stopping a blade root end edge of the used blade; and (e) a push button including a pair of projection pieces each of which pushes down the used blade surface on both sides of the blade mounting part, the surface being pushed down until it makes contact with a stopper provided on the cover part and thereby allows the blade root end edge to be engaged with the angle notch of the stopper stepped part.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 6 is a bottom plan view of the cover part of FIG. 4;

FIG. 7 is a cross sectional view along a line VII—VII of FIG. 6;

FIG. 8 is a front view illustrating an opening part of the apparatus of FIG. 1;

DESCRIPTION OF THE PREFERRED EMBODIMENT

An embodiment of a blade removal apparatus of the present invention will be described with reference to the accompanying drawings.

Figure 1:
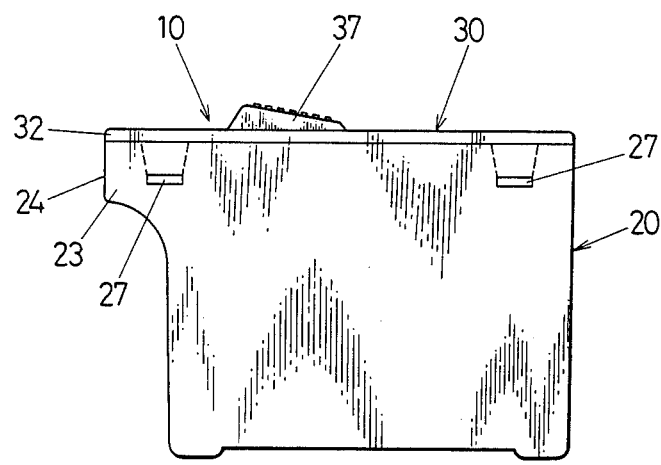
FIG. 1 is a front view illustrating a blade removal apparatus for a changeable blade scalpel according to the present invention.
Figure 2:
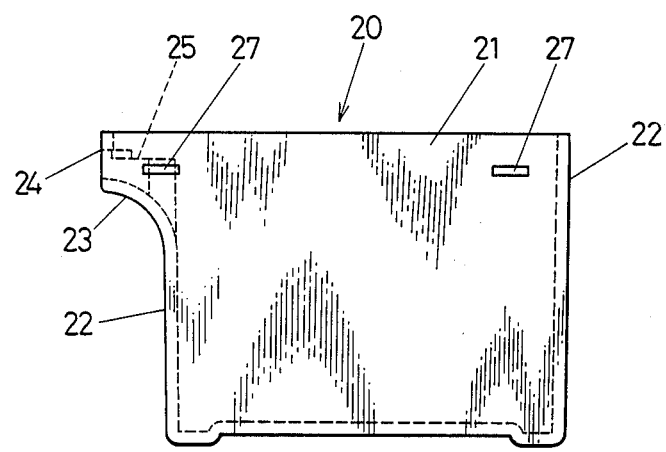
FIG. 2 is a front view illustrating a box part for use in the blade removal apparatus of the present invention.
Figure 3:
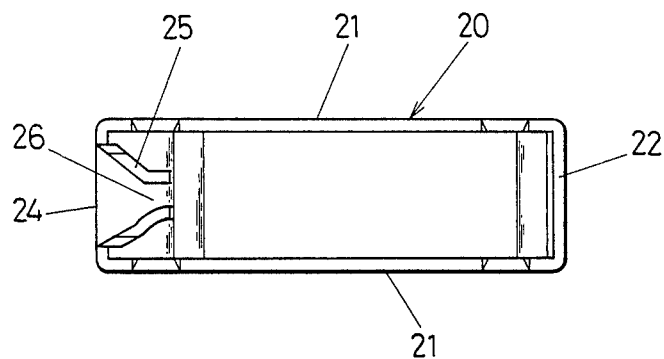
FIG. 3 is a plan view of the box part of FIG. 2.
Figure 4:
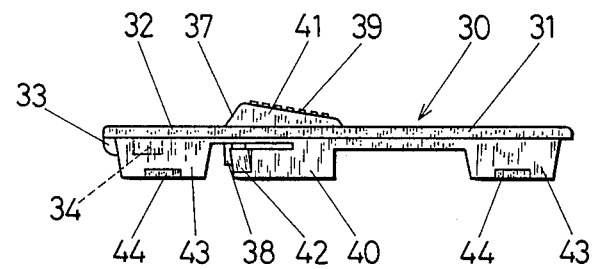
FIG. 4 is a front view illustrating a cover of the apparatus of FIG. 1.
Figure 5:
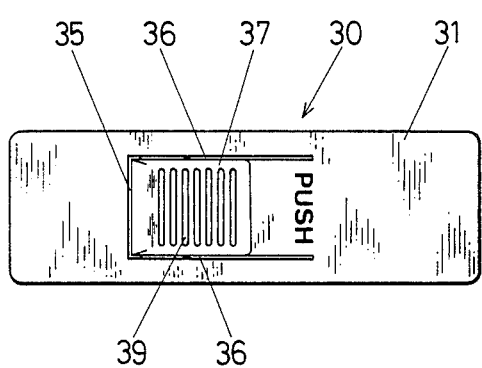
FIG. 5 is a top plan view of the cover part of FIG. 4.
Figure 9:
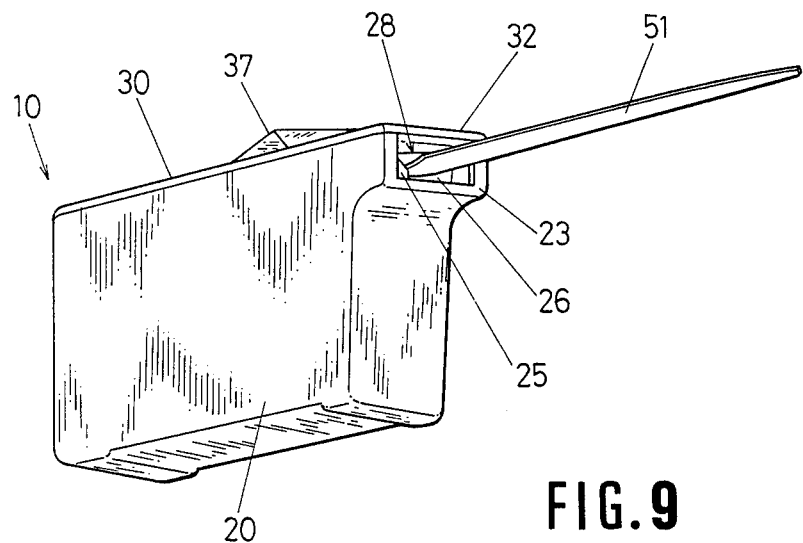
FIG. 9 is a perspective view illustrating the removal apparatus into which a blade part of a changeable blade scalpel has been inserted.

As shown in FIG. 1, a removal apparatus 10 for a changeable blade scalpel includes a closed-bottom box part 20 having a rectangular cross section thereof. The box part 20 made for example of a plastic material has front and rear walls 21 as well as a pair of side walls 22 as shown in FIGS. 2 and 3. The box part 20 furthermore has the upper part of one side wall 22 thereof which partly forms an acceptor part 23 projecting from the side wall 22. The acceptor part 23 includes a guide edge 25 at a position spaced below the upper end thereof by a prescribed amount to leave an upper space 29, which guide edge is tapered to become narrower as it goes interiorly from the front end 24. The guide edge 25 has a lower groove 26 provided parallely to the guide groove 25 at the inside end thereof through which a blade mounting part 53 of a scalpel handle 52 of a changeable blade scalpel 51 described later smoothly passes. A cover part 30 for covering the opening through the upper surface of the box part 20 has a rectangular plate part 31 as shown in FIGS. 4 to 6. The plate part 31 is adapted to have a visored part 32 at a position above the acceptor part 23 upon covering the opening through the upper surface of the box part 20. A stopping stepped part 33 having a prescribed thickness is formed on the lower surface of the visored part 32, on the inside surface of which stepped part 33 an angle notch 34 is formed which is capable of making contact with an acute angle blade root end edge 66 of a blade 61. The cover part 30 has a transverse cut 35 extending at right angle to its longitudinal direction near the stopping stepped part 33 from the longitudinal center of the cover part. The cover part furthermore has a pair of longitudinal cuts 36 of a prescribed length extending away from the stopping stepped part 33 from both ends of the transverse cut 35 and perpendicularly thereto. The portion surrounded by these three notches forms a push button 37 rockable vertically. The push button 37 projects upwardly of the plate part 31 forming a triangular shape and has a pair of projection pieces 38 projecting downwardly and formed on the end part of the push button 37 on the side of the transverse cut 35 at a larger interval than the breadth of the blade mounting part 53 of the changeable blade scalpel 51. Moreover, the push button 37 has a number of non-slip riased portions 39 provided on the upper surface thereof. The cover part 30 includes a pair of stoppers 40 facing downwardly and disposed on the lower surface thereof outside both the longitudinal cuts 36. Each stopper 40 is fixedly mounted at one end thereof in the vicinity of the starting end of the longitudinal cuts 36, while it cantilevers in the other end thereof from the fixed portion of the stopper toward the transverse cut 35 leaving a prescribed space between it and the lower surface of the cover part 30. Moreover, stopping parts 42 are provided on the tip ends of the stoppers 40, which have substantially triangular flat cross sections and mutually project toward the opposed part 42, for stopping the push button 37 by being engaged by the lower surface of the side plate 41 of the push button 37 when pushing down the push button 37 to a prescribed position. Furthermore, the cover part 30 includes downward guide plate 43 respectively formed on the side lower surfaces of both longitudinal ends thereof, which guide plates respectively have stopper pieces 44 provided on the lower ends thereof projecting externally. When the cover part 30 is fitted to the upper part of the box part 20, the respective stopper pieces 44 of the guide plates 43 disposed on both sides of the cover 30 are engaged in stop holes provided in the front and rear walls 21 of the box part 20, whereby the cover part 30 is securely fixed on the box part 20. When the cover part 30 is integrally fixed with the box part 20 as described above, a T-shaped gap 28 composed of the lower groove 26 and the upper space 29 is formed between the acceptor part 23 of the box part 20 and the visored part 32 of the cover part 30 as shown in FIG. 8.

The changeable blade scalpel 51 becomes thinner and slightly protrudes at the tip end of the scapel handle 52 thereof to form a blade mounting part 53. A blade groove 54 is provided in the blade mounting part 53 on the tip end thereof, in which a narrow hole part 63 having a narrower width and located toward the tip of the blade 61 among the longitudinal holes formed in the change blade 61 is fitted. Moreover, the longitudinal holes of the change blade 61, those 64 located more closely to the blade root part 62 than to the fine hole 63 respectively have a wider width than the fine hole 63. Here, designated at 65 is a cutting edge.

In succession, to mount the change blade 61 on the change blade scalpel 51, the wider hole 64 of the change blade 61 is aligned to the blade mounting part 53 of the scalpel handle 52, and thereafter the fine hole 63 of the change blade 61 is fitted in the blade groove 54 of the blade mounting part 53 while the acute-angled blade root end edge 66 is pushed in until it makes close contact with the slanted stepped part 55 of the scalpel handle 52. Hereby, the change blade 61 is fixedly mounted on the scalpel handle 52.

Subsequently, operation of the embodiment will be described.

Figure 10:
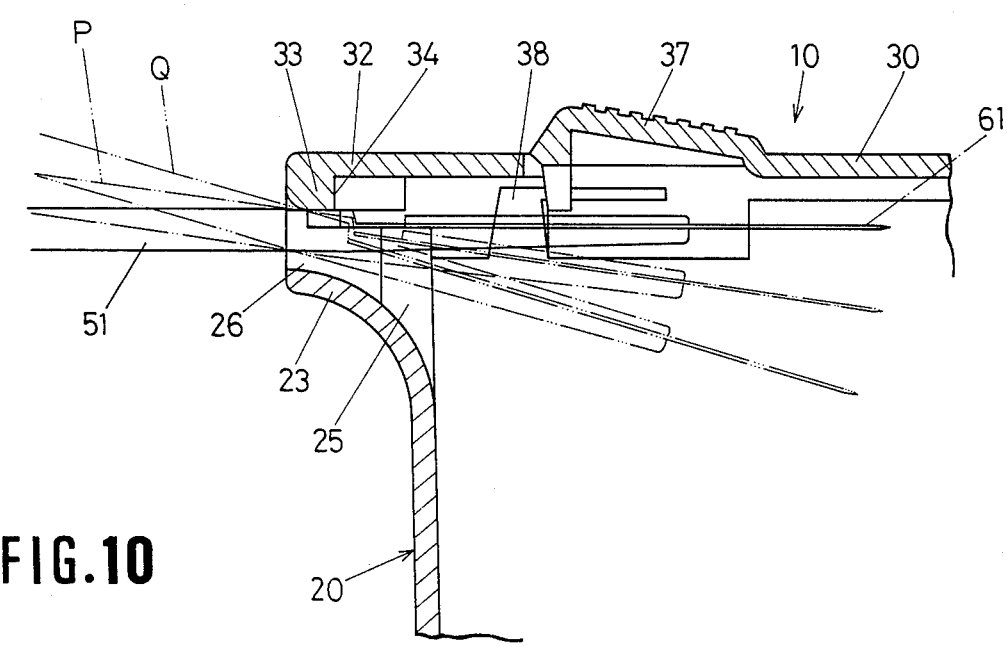
FIG. 10 is a sectional view showing steps in removing a change blade by making use of the removal apparatus of FIG. 1.
Figure 11:
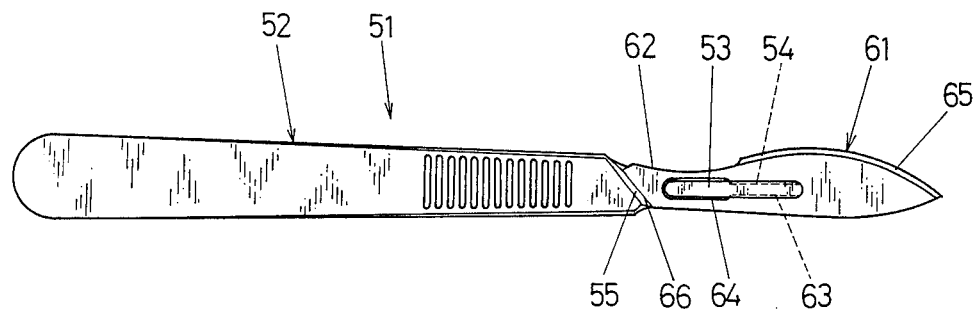
FIG. 11 is a front view illustrating a changeable blade scalpel.
Figure 12:
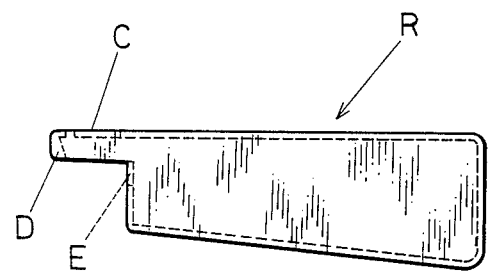
FIG. 12 is a front view illustrating a prior removal apparatus.
Figure 13:
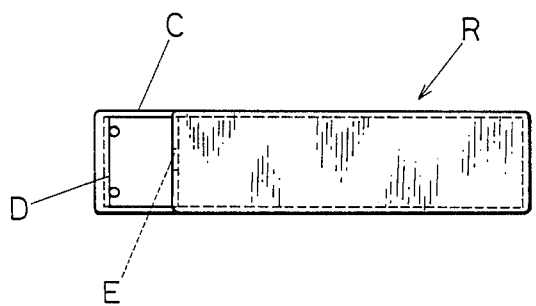
FIG. 13 is a plan view illustrating the prior removal apparatus of FIG. 12.
Figure 14:
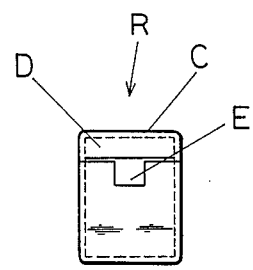
FIG. 14 is a side view illustrating the prior removal apparatus of FIG. 12.
Figure 15:
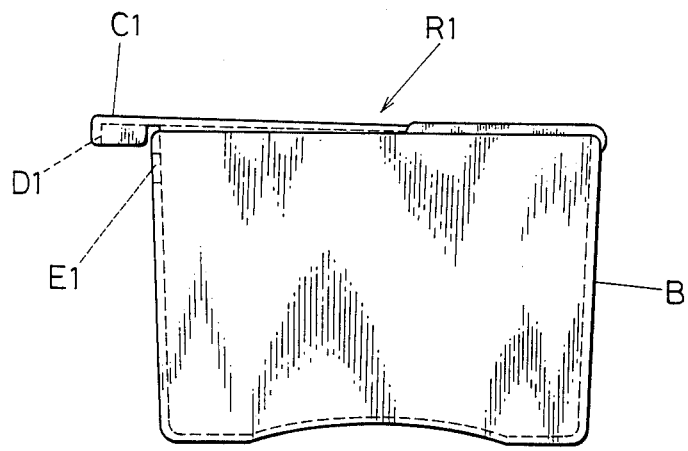
FIG. 15 is a front view illustrating another prior removal apparatus.
Figure 16:
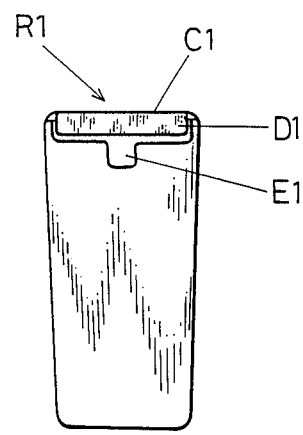
FIG. 16 is a side view of FIG. 15.

To change a waste blade of the change blade scalpel 51, the change blade scalpel 51 is turned up (the slanted stepped part 55 is turned up, with which the blade root end edge 66 makes contact.), and the change blade 61 thereof is inserted into the T-shaped gap 28 of the acceptor part 23 of the removal apparatus. Then, the blade mounting part 53 of the scalpel handle 52 is pushed into the removal apparatus 10 with the change blade 61 supported on the guide edge 25 until the base part of the blade mounting part 53 makes contact with the guide edge 25. Thereupon, the change blade scalpel 51 is kept substantially horizontal (refer to FIG. 10). In succession, when the push button 37 is depressed, both sides of the blade mounting part 53 of the change blade 61 are pushed down while allowing a pair of projection pieces 38 located on the lower part of the bottom 37 straddle the blade mounting part 53. Then, when these pieces are pushed down until the upper surface of the scalpel handle 52 makes contact with the lower surface of the tip end of the visored part 32 of the cover part 30, the blade mounting part 53 is slightly lowered, whereby the changeable blade scalpel 51 is brought to a position P shown in FIG. 10. When the push button 37 is further pushed down to cause the lower surface of the side plate 41 to make contact with the respective stopper part 42 of the respective stoppers 40, the upper surface of the scalpel handle 52 is forced against the lower surface of the tip end of the visored part 32 of the cover part 30 to take a position Q of FIG. 10, while it causes the blade root part 62 of the blade 61 to float from the slanted stepped part 55 of the scalpel handle 52. Thereby, the wide hole part 64 is caused to move away from the blade mounting part 53, and the blade root end edge 66 is engaged with the angle notch 34 formed in the visored part 32 of the cover part 30. In this situation, when the scalpel handle 52 is pulled out of the removal apparatus 10 while being slightly pulled up, the blade mounting part 53 of the scalpel handle 52 is disengaged from the small hole 63, because the blade root end edge 66 of the change blade 61 has been stopped by the angle notch 34. Thereby, the scalpel 52 is pulled out from the removal apparatus 10, and the change blade 61 remains in the removal apparatus 10 and falls onto the bottom of the box part 20 by relaxing the push-down force of the push button 37.

The width of the lower groove 26 formed by the guide edge 25 of the box part 20 is such as to permit the blade mounting parts 53 of the scalpel handles 52 of various sizes to pass therethrough, and hence the removal apparatus 10 can remove the blades 61 of the various types of the changeable blade scalpels 51. Furthermore, the removal apparatus 10 may be operated only by allowing part of the blade 61 of the blade scalpel 51 to be inserted into the T-shaped gap 28 thereof and the push button 37 actuated to force down the change blade 61. Thus, the change blade 61 can be extremely easily removed.

Although a certain preferred embodiment has been shown and described, it should be understood that many changes and modifications may be made therein without departing from the scope of the appended claims.

What is claimed is:

1. A blade removal apparatus for a changeable blade scalpel in which a blade is removably mounted on a scalpel handle by fitting a mounting hole formed in the blade over a blade mounting part having a narrow width provided on the tip end of the scalpel handle, said blade removal apparatus comprising:
    a box part having an open top and a side wall and an acceptor part projecting laterally from the upper part of said side wall;
    a cover part closing said open top and having a visored part extending over said acceptor part;
    a guide edge means on said acceptor part defining a lower gap tapered so as to become narrower as it extends to the inside of said box part and into which blade mounting parts of changeable blade scalpels of various types can be inserted;
    said cover part having a stopping stepped part defining an upper gap between the lower surface of said visored part and said guide edge and into which upper gap a blade on a scalpel is insertable, said stopping stepped part further having an angle notch engageable by a blade root and edge on a blade, a pair of stoppers projecting from the lower side of said cover part on both sides of said lower gap, and a push button which can be pushed down from said cover into said box part having a pair of projection pieces which, when said push button is pushed down, make contact with said stoppers for forcing the blade surface located on both sides of the blade mounting part on the scalpel down for lifting the blade root end edge of the blade and thereby causing the blade root end edge to be engaged with said angle notch of said stopping stepped part.

2. A blade removal apparatus according to claim 1 wherein said box part is made of a plastic material.

3. A blade removal apparatus according to claim 1 wherein said push button has a plurality of non-slip projection portions on the upper surface thereof.

* * * * *